(12) United States Patent
Wolter

(10) Patent No.: US 10,493,198 B2
(45) Date of Patent: Dec. 3, 2019

(54) PUMP DEVICE

(71) Applicant: OLYMPUS WINTER & IBE GMBH, Hamburg (DE)

(72) Inventor: Michael Wolter, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 125 days.

(21) Appl. No.: 15/328,111

(22) PCT Filed: Jul. 21, 2015

(86) PCT No.: PCT/EP2015/066615
§ 371 (c)(1),
(2) Date: Jan. 23, 2017

(87) PCT Pub. No.: WO2016/012432
PCT Pub. Date: Jan. 28, 2016

(65) Prior Publication Data
US 2017/0209639 A1    Jul. 27, 2017

(30) Foreign Application Priority Data

Jul. 23, 2014 (DE) .......... 10 2014 214 359

(51) Int. Cl.
| | | |
|---|---|---|
| *A61M 3/02* | (2006.01) | |
| *A61B 5/00* | (2006.01) | |
| *A61B 1/00* | (2006.01) | |
| *A61B 1/015* | (2006.01) | |
| *A61G 13/00* | (2006.01) | |
| *A61G 13/06* | (2006.01) | |
| *G05D 16/20* | (2006.01) | |
| *A61B 34/20* | (2016.01) | |

(52) U.S. Cl.
CPC ....... *A61M 3/0216* (2014.02); *A61B 1/00006* (2013.01); *A61B 1/015* (2013.01);
(Continued)

(58) Field of Classification Search
CPC ........ A61G 13/06; A61B 1/015; A61B 5/704; A61M 3/0216; A61M 2205/3331; A61M 3/0266; A61M 5/1415; A61M 2209/084
See application file for complete search history.

(56) References Cited

U.S. PATENT DOCUMENTS

| | | | |
|---|---|---|---|
| 4,795,424 A | | 1/1989 | Burner |
| 5,280,789 A | * | 1/1994 | Potts ................. A61B 5/02152 33/379 |

(Continued)

FOREIGN PATENT DOCUMENTS

| | | |
|---|---|---|
| CN | 201921065 U | 8/2011 |
| CN | 203100726 U | 7/2013 |

(Continued)

OTHER PUBLICATIONS

English translation of DE 10 2007 06220.*

(Continued)

*Primary Examiner* — Emily L Schmidt
(74) *Attorney, Agent, or Firm* — Scully, Scott, Murphy & Presser, P.C.

(57) ABSTRACT

A pump device for use with an operating table in an operating room. The pump device including: a pump for pumping a rinsing liquid through a pump tube, and a controller configured to determine a height adjustment of the operating table in the operating room and control the pump pressure of the pump based on the detected height adjustment.

11 Claims, 3 Drawing Sheets

(52) U.S. Cl.
CPC .............. *A61B 5/704* (2013.01); *A61B 34/20* (2016.02); *A61G 13/0018* (2013.01); *A61G 13/06* (2013.01); *A61M 3/0254* (2013.01); *A61M 3/0258* (2013.01); *G05D 16/2066* (2013.01); *A61B 5/4836* (2013.01); *A61G 2203/10* (2013.01); *A61G 2203/36* (2013.01); *A61M 2205/3313* (2013.01); *A61M 2205/3317* (2013.01); *A61M 2205/3327* (2013.01); *A61M 2205/3331* (2013.01); *A61M 2205/3375* (2013.01); *A61M 2205/581* (2013.01); *A61M 2205/583* (2013.01)

(56) References Cited

U.S. PATENT DOCUMENTS

| | | | |
|---|---|---|---|
| 5,586,973 | A | 12/1996 | Lemaire et al. |
| 6,522,908 | B1 | 2/2003 | Miyashita et al. |
| 2005/0077852 | A1 | 4/2005 | Treon |
| 2011/0251548 | A1* | 10/2011 | Thoe ................. A61F 9/007 604/31 |
| 2012/0042451 | A1 | 2/2012 | Jones et al. |
| 2013/0090572 | A1* | 4/2013 | Peliks ................. A61B 5/4325 600/591 |
| 2014/0276639 | A1* | 9/2014 | Tarkeshian .......... A61M 3/0237 604/521 |

FOREIGN PATENT DOCUMENTS

| | | |
|---|---|---|
| DE | 3540326 A1 | 5/1987 |
| DE | 4024676 A1 | 2/1992 |
| DE | 102007062200 A1 | 9/2008 |

OTHER PUBLICATIONS

International Search Report dated Oct. 1, 2015 issued in PCU/EP2015/066615.
English Abstract of EP0469266 A1, dated Feb. 5, 1992.

* cited by examiner

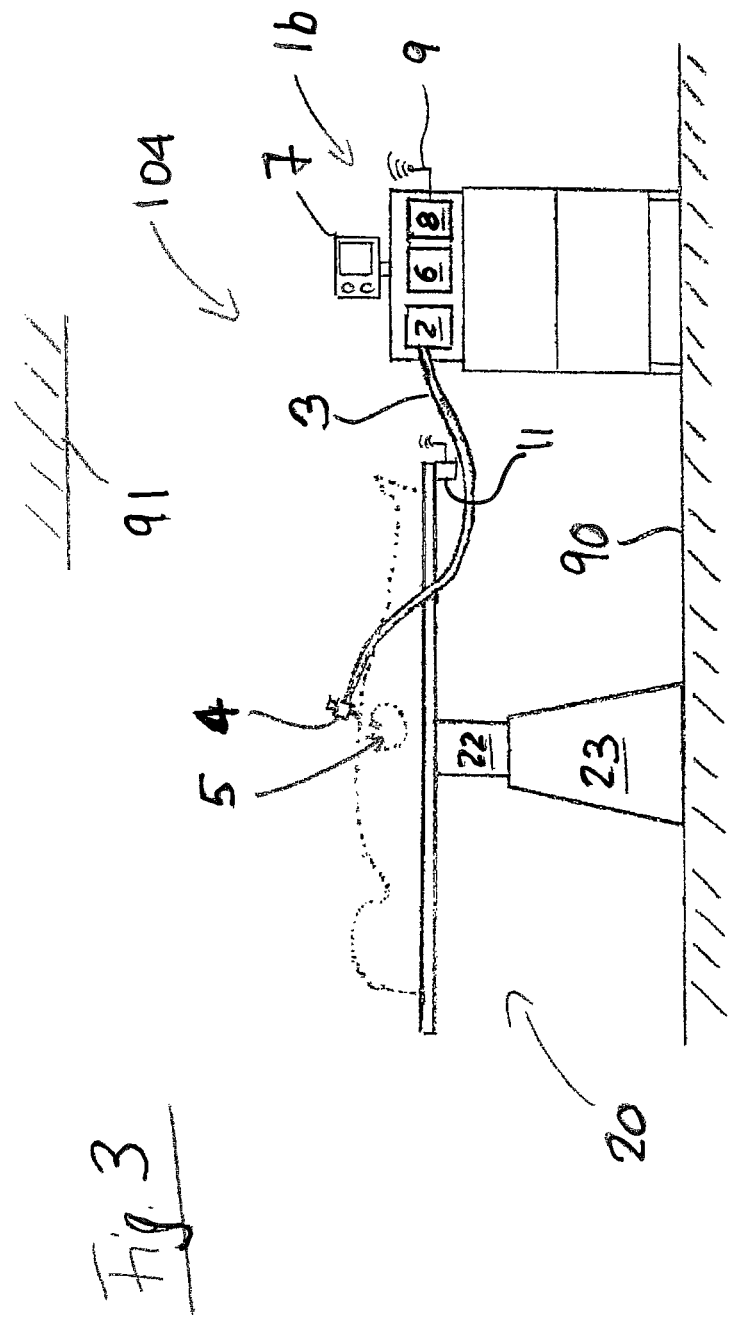

PUMP DEVICE

CROSS-REFERENCE TO RELATED APPLICATION

The present application is based upon and claims the benefit of priority from PCT/EP2015/066615 filed on Jul. 21, 2015, which claims benefit to DE 10 2014 214 359.4 filed on Jul. 23, 2014, the entire contents of each of which are incorporated herein by reference.

BACKGROUND

Field

The present disclosure generally relates to pump devices for use in operating rooms and in particular for supplying rinsing liquid during minimally invasive surgery, and to arrangements comprising corresponding pump devices.

Prior Art

In the field of medical technology for operating rooms, pumps are often present as part of medical apparatuses or as separate units connected to medical apparatuses. In the field of minimally invasive surgery, it is known to introduce rinsing liquid into the surgical site or into a body cavity encompassing the surgical site with the aid of a pump. The body cavity is hereby filled with and expanded by the rinsing liquid in such a way that the surgical site can be clearly seen by the operating surgeon, for example, through an endoscope. The rinsing liquid can be supplied and, if necessary, removed through the endoscope itself. It is also possible, however, for the rinsing liquid to be introduced into the surgical site through devices which are separate from the endoscope, such as, for example, catheters.

During the rinsing of a surgical site, it is of immense significance that a pressure of the rinsing liquid in the surgical site specified by the operating surgeon be maintained as exactly as possible. If the pressure drops below the specified value, the body cavity encompassing the surgical site can collapse. If a surgical procedure is carried out in such a moment using a suitable instrument, there is a risk that the tissue forming the body cavity will come into contact with the surgical instrument and become damaged thereby. If the pressure is above the specified value, the rinsing liquid can penetrate the tissue and/or the blood circulation of the patient, which can result in hypotonic hyper hydration with cardiovascular strain up to acute right ventricular failure. Such serious complications absolutely must be avoided.

In order to avoid corresponding complications, it is known in the prior art to hold the pump pressure of the pumps for rinsing liquid at a specified value as precisely as possible, i.e., to hold said pressure constant, and to balance inflowing and outflowing rinsing liquid. The purpose of the initially mentioned measure is to hold the pressure at the surgical site as constant as possible; the balancing of the rinsing liquid enables the control that no rinsing liquid penetrates the tissue and/or the blood circulation of the patient.

The disadvantage of this prior art is that changes in the basic conditions, which occur during a surgical procedure and influence the required and allowable pressure at the surgical site, are not regularly taken into account. In the prior art, changes of this type require, in principle, that the value specified for the pump pressure be changed manually, which is often not thought of during operations, however, and which can result in the aforementioned complications.

The laid-open application DE 40 24 676 A1 describes a device for rinsing the bladder, in which the necessary rinsing pressure is generated solely by means of an elevated placement of the rinsing-liquid reservoir. The device comprises a pressure regulator which is supposed to be disposed so as to be stationary with respect to the surgical site (e.g., by placing the pressure regulator on the abdomen of the patient), in order to thereby avoid any change in pressure which could result in a change in the height difference between the pressure regulator and the bladder. Given that the pressure regulator can also be disposed in a similar position with respect to the bladder in different patients, it is possible to work with patient-independent empirical values when adjusting the pressure regulator. The disadvantage of this prior art is that the pressure regulator comes into direct contact with the rinsing liquid and, therefore, must be regularly sterilized.

SUMMARY

The pump devices disclosed herein, which are for use in operating rooms and which can be used for supplying rinsing liquid during minimally invasive surgery, address the disadvantages of the prior art such that they no longer occur or do so only to a reduced extent.

Accordingly, a pump device is provided for use in operating rooms, the pump device comprising a pump unit having a pump for pumping a rinsing liquid through a pump tube, and a control unit for controlling the pump pressure of the pump unit, wherein the pump device comprises a detection module for detecting a height adjustment of the operating table in the operating room.

Also provided is an arrangement comprising the pump device and an operating table.

The pump device recognizes that the pressure, for example, of the rinsing liquid at a surgical site changes during minimally invasive surgery after the initial specification of a pump pressure (e.g., by the operating surgeon), in particular due to a height adjustment of the operating table on which the patient, who will be operated on, is lying. In this case, the pressure changes result from changes in the static pressure due to the change in the height difference between the pump and the surgical site. These pressure changes can result in critical pressures at the surgical site, at which the tissue enclosing the surgical site collapses or rinsing liquid enters the tissue and/or the blood circulation of the patient.

In order to avoid complications of this type while simultaneously making it possible, however, for the operating surgeon to also arbitrarily adjust the height of the operating table during the operation in order to be able to work as ergonomically as possible, it is provided that the pump device comprises a detection module for detecting a height adjustment of the operating table. Given that the pump device comprises a detection module of this type, it is possible to react to an adjustment of the height of the operating table, as is explained below. An element which is provided in addition to simple pump devices, comes into contact with the rinsing liquid and, therefore, must be regularly disinfected, is not provided.

In order to be able to detect a height adjustment of the operating table, it can be provided that the detection module is configured to receive or request output information from control electronics of the operating table in order to detect a corresponding height adjustment on the basis of the output information.

Modern operating tables often comprise electric motors for height adjustment and, if necessary, further adjustment possibilities, and associated control electronics which can also be configured for incorporation into a data network which connects various devices in an operating room. The individual devices in the operating room can communicate with each other and exchange data via such a data network. The control electronics of the operating table can thereby regularly deliver information regarding the set height of the operating table.

Accordingly, the detection module of the pump device can communicate with the control electronics of the operating table via a data network or, alternatively, via a direct wireless or wired connection. The output information transmitted from the control electronics of the operating table to the detection module of the pump device can contain, for example, information regarding the present absolute height of the operating table, information regarding an instantaneous vertical movement of the operating table, or the like. The output information provided by the control electronics of the operating table can be suitable for being able to unambiguously detect a height adjustment of the operating table, based solely on the output information. This can also be achieved by detecting a change over time of parameters, for example, the height of the operating table.

The detection module can be configured for receiving corresponding output information. In this case, the control electronics of the operating table can transmit information to the detection module regularly or as needed—such as during an actual adjustment of the height of the operating table—regarding the height of the operating table and/or its adjustment, which information can then be further processed in said detection module. Alternatively or additionally, it is possible for the detection module to request the corresponding information from the control electronics of the operating table at regular intervals.

In order to be able to detect an adjustment of the height of the operating table, the pump device can comprise, alternatively or additionally, a telemetry unit which is designed for detecting the height or an adjustment of the height of the operating table, wherein the detection module can be configured for receiving or requesting output information from the telemetry unit in order to detect a corresponding height adjustment on the basis of the output information.

A telemetry unit for detecting the height or an adjustment of the height of the operating table can comprise a distance-measuring unit and/or an acceleration sensor.

In the case of a distance measurement, a telemetry transmitter can be disposed on the height-adjustable part of the operating table and can comprise a distance-measuring unit which can determine the distance to the floor and/or to the ceiling of the operating room or to at least one reference module which is stationary with respect to the non-height-adjustable part of the operating table. The distance to the floor or the ceiling or to the at least one reference module can take place, for example, via a transit-time measurement of electromagnetic, such as optical or acoustic waves, wherein the frequency of the waves can lie outside the visible or audible spectrum. In the case of at least one reference module, the distance measurement can also take place via a field-strength measurement, provided the at least one reference module generates a suitable measurable field.

By determining the particular distance to the floor and to the ceiling or to at least two reference modules, which are disposed separately from each other, the particular measurements can also be cross-checked and, in this way, the risk of measuring errors can be reduced. A check of the measurement results can take place, for example, in that the sum of the two measured distances to the floor and the ceiling or to two reference modules must correspond to the distance between the floor and the ceiling or to the two reference modules. If this is not the case, at least one of the two measurements is faulty and a warning can be output, if necessary. A corresponding check and/or output of a warning can take place directly in the telemetry transmitter or can take place downstream, for example, by means of the receiving module or a separate checking module.

It is also possible for at least one reference module to be disposed on the height-adjustable part of the operating table and for the telemetry transmitter to be disposed so as to be stationary with respect to the non-height-adjustable part of the operating table, e.g., the base of the operating table.

It is also possible for the telemetry unit to comprise an acceleration sensor. If the telemetry unit is disposed on the height-adjustable part of the operating table, an adjustment of the height of the operating table can be detected via the acceleration sensor.

Further, the detection module of the pump device can communicate with the telemetry transmitter via a wired or a wireless connection. The output information transmitted, in this case, from the telemetry transmitter to the detection module of the pump device can correspond to the output information from control electronics of an operating table in this case. Reference is therefore made to the comments presented above.

The detection module can be configured for receiving corresponding output information. In this case, the telemetry transmitter can transmit information to the detection module regularly or as needed—i.e., such as during an actual adjustment of the height of the operating table—regarding the height of the operating table and/or its adjustment, which information can then be further processed in said detection module. Alternatively or additionally, it is possible for the detection module to request the corresponding information from the telemetry transmitter at regular intervals.

The pump device can be configured for outputting an optical or acoustic warning signal upon detection of a height adjustment of the operating table. For this purpose, the pump device can comprise one or multiple suitable signal generators. It is also possible, however, for the pump device to comprise a communication module for outputting an optical or acoustic warning signal to an external device which has a suitable signal generator. The external device with which the pump device communicates in order to output warnings can be, for example, a device which is used during the operation and is located within the field of view of the operating surgeon to a greater extent than the pump device, such as, e.g., a vital-function monitor.

The detection module can be configured not only for detecting a height adjustment, but also so as to be capable of detecting the height difference of the height adjustment. In other words, the detection module can not only be able to detect the fact that the height of the operating table has been adjusted, but should also be able to detect the direction and the amount of the height adjustment. The height difference can be determined, such as, on the basis of the height of the operating table at the point in time of the initial setting of the pump pressure. The height difference can also be ascertained on the basis of a permanently established reference height.

The above-described variants for detecting the height adjustment of the operating table via the control electronics of the operating table and/or a telemetry unit can be suitably configured for detecting the height difference.

The pump device can comprise a display for the height difference of the height adjustment. The displayed height difference can then alert the operating surgeon as to whether the specified value for pump pressure must be changed and, if so, to what extent.

The control unit can be designed for changing the pump pressure depending on the height difference of the height adjustment. Proceeding from the initial setting of the pump pressure carried out by the operating surgeon at an initial height of the operating table, the control unit can then regulate the pump pressure in such a way that it is ensured that the pressure of the rinsing liquid will remain the same even if the height of the operating table in the operating room is adjusted. Alternatively, it is possible for the operating surgeon to specify the pump pressure already based on a reference height and for the control unit to adjust the pump pressure according to the height difference.

The relationship between the height difference, the height adjustment, and the change in the pump pressure can be linear. This relationship corresponds to equation (1):

$$\Delta p = a \times \Delta h \times 10^4 \frac{\text{Pa}}{\text{m}} \qquad (1)$$

wherein $\Delta p$ corresponds to the change in the pump pressure and $\Delta h$ corresponds to the height difference of the height adjustment. The term $$10^4 \frac{\text{Pa}}{\text{m}}$$

(which corresponds to $$\frac{\text{mbar}}{\text{cm}})$$

is a conversion factor which at least approximately reflects the static pressure of a typical rinsing liquid, such as a water-based rinsing liquid, depending on the height of the column of liquid. The correction factor a can be between 0.8 to 1.2, such as between 0.9 and 1.1 and, further can be 1. The conversion factor and the correction factor can also be combined into one factor.

The detection module can comprise a light element—such as a laser—for projecting a calibration plane, a calibration scale, or at least one calibration point onto the operating table or onto the patient who is lying on the operating table. The calibration scale can comprise multiple parallel lines, for example, separated from each other by a predetermined distance, such as 1 cm. Given that a corresponding calibration plane, a calibration scale, or at least one calibration point is projected, a height adjustment of the operating table can be visualized, in order to alert the operating surgeon to the need to readjust the pump pressure. This is can be effective when the calibration plane, the calibration scale, or the at least one calibration point is projected in such a way that the surroundings of the surgical site are free from projections of the light element in the initial height adjustment of the operating table, but when the height of the operating table is adjusted, the projections move into these surroundings which can be within the field of view of the operating surgeon.

Reference is made to the comments presented above for the explanation of the arrangement.

BRIEF DESCRIPTION OF THE DRAWINGS

The invention will now be described, by way of example, on the basis of advantageous embodiments with reference to the attached drawings. In the drawings:

FIG. 3 illustrates a variant of the exemplary embodiment of FIG. 2.

DETAILED DESCRIPTION

Figure 1:
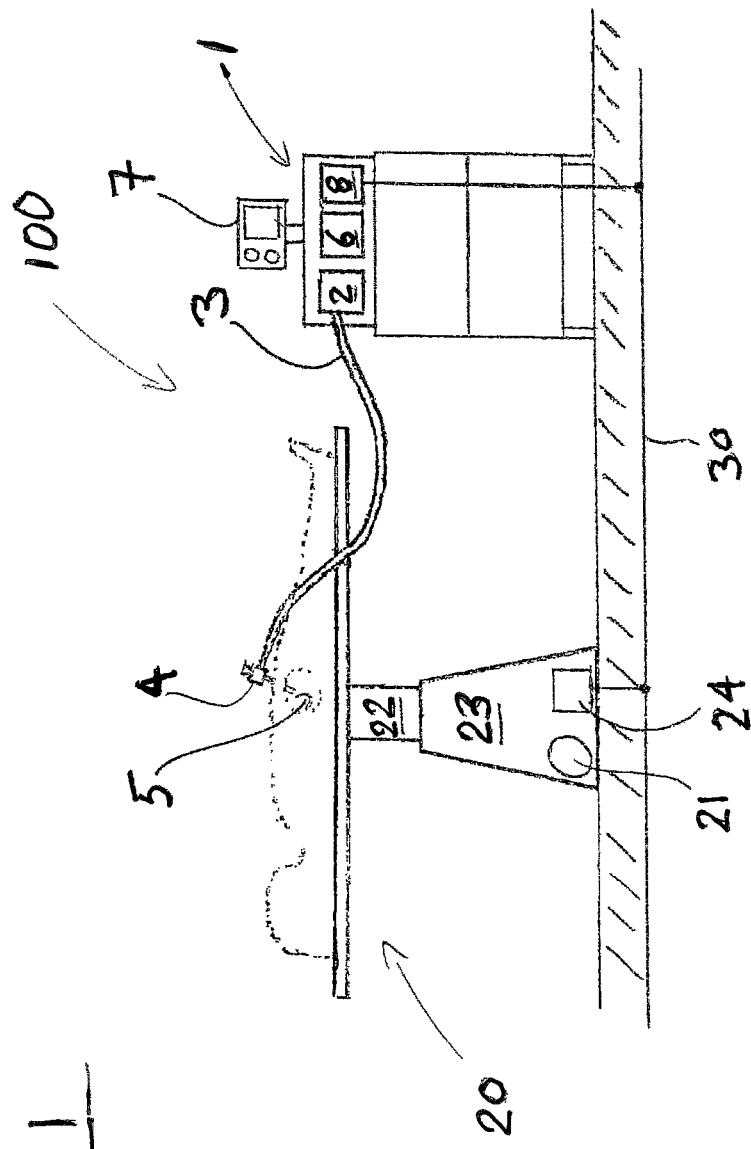
FIG. 1 illustrates a first exemplary embodiment of an arrangement comprising a first exemplary embodiment of a pump device.

FIG. 1 illustrates a first exemplary embodiment of an arrangement 100 comprising a first exemplary embodiment of a pump device 1 and a height-adjustable operating table 20.

The pump device 1 comprises a pump unit 2 for pumping a rinsing liquid through a pump tube 3 which is fastened via one end thereof to the pump unit 2. At the other end thereof, the pump tube 3 is connected to an endoscope 4. The endoscope 4 can be introduced into a body cavity of a patient for a minimally invasive procedure, wherein the body cavity is filled with and expanded by the rinsing liquid, and therefore the surgical site 5, which is exposed as a result, can be clearly seen by the operating surgeon through the endoscope 4.

The pump device 1 also comprises a controller 6 for controlling the pump pressure of the pump unit 2. The controller 6 is configured for regulating the pump pressure, i.e., the pressure generated by the pump unit 2 on the pressure side, to a specified value. The specified value can be set via a user interface 7. The control or regulation of the pump unit 2 can take place on the basis of stored operating curves or on the basis of a pressure sensor (not illustrated) disposed on the pressure side of the pump unit 2.

In addition, a detection module 8 for detecting a height adjustment of the operating table 20 is provided on the pump device 1. The detection module 8 is either configured together or separately from the controller 6 (singularly or collectively referred to in the claims as "a controller").

The height of the operating table 20 is adjustable via a motor 21. In this case, a height-adjustable part 22 of the operating table 20 is displaced relative to a non-adjustable part—the base 23—of the operating table 22. The displacement of the two parts 22, 23 relative to each other is achieved via the motor 21 which is controlled by the control electronics 24.

The control electronics 24 are connected to a data network 30 via which various apparatuses in the operating room (not illustrated) communicate with each other and can exchange data. The pump device 1 and the detection module 8 of the pump device 1 are also connected to this data network 30.

The control electronics 24 of the operating table 20 are configured in such a way that, in the event that the height of the operating table 20 is adjusted, a height-adjustment signal, as output information, is transmitted to the detection module 8 of the pump device 1. The control electronics 24 are also configured for outputting, when queried, the absolute height of the operating table 20 or the relative position between the two parts 22, 23 of the operating table 20 which are movable relative to each other.

The detection module 8 is configured both for receiving the output information of the height-adjustment signal from the control electronics 24 and for requesting the output information regarding the absolute height of the operating table 20 from the control electronics 24.

In the exemplary embodiment shown, the detection module 8 of the pump device 1 has at least two operating modes which can be set via the user interface 7.

In a first operating mode, the detection module 8 detects that the height of the operating table 20 has been adjusted, on the basis of the height-adjustment signal transmitted as output information from the control electronics 24, and outputs a warning signal via the user interface 7. The warning signal can be optical and/or acoustic. By way of the warning signal, the operating surgeon is prompted to adjust the pump pressure of the pump unit 2 via the control unit 6 and the user interface 7 in such a way that an allowable pressure prevails at the surgical site 5.

In a second operating mode, the detection module 8 requests, at regular time intervals, output information regarding the absolute height of the operating table 20 from the control electronics 24 thereof. The time intervals of the requests can be selected in a variable way. In particular, upon receipt of a piece of output information which includes a height-adjustment signal, the time interval between two requests can be selected to be short, while the interval for the remainder of the time is selected to be greater.

The detection module 8 is configured, in this case, for determining the height difference of the height adjustment, i.e., the difference in the height of the operating table 20 at an arbitrary point in time and at the point in time at which the pump pressure of the pump unit 2 was initially set, on the basis of the requested output information and proceeding from the height of the operating table 20 at the point in time at which the pump pressure of the pump unit 2 was initially set at the user interface 7. Alternatively, the height difference can also be determined relative to an established reference height.

The controller 6 is configured for adjusting the pump pressure of the pump unit 2 depending on the height difference determined by the detection module 8, and therefore the pressure of the rinsing liquid at the surgical site 5 remains constant despite the height adjustment of the operating table 20. For this purpose, the pump pressure is adjusted according to the equation (1):

$$\Delta p = a \times \Delta h \times 10^4 \frac{Pa}{m} \quad (1)$$

In this case, $\Delta p$ is the required change in the pump pressure and $\Delta h$ is the height difference determined by the detection module 8. The term $$10^4 \frac{Pa}{m}$$

(which corresponds to $$\frac{mbar}{cm})$$

is a conversion factor; the correction factor a is in the exemplary embodiment 1 shown.

Figure 2:
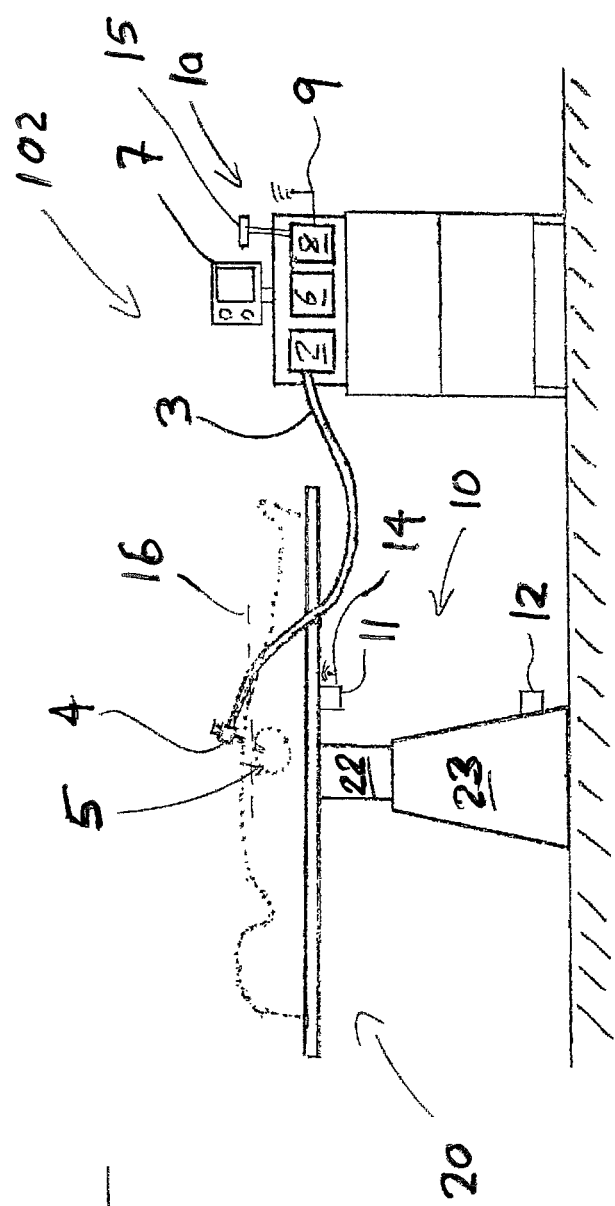
FIG. 2 illustrates a second exemplary embodiment of an arrangement, comprising a second exemplary embodiment of a pump device.

FIG. 2 illustrates a second exemplary embodiment of an arrangement 102, comprising a second exemplary embodiment of a pump device 1 and a height-adjustable operating table 20.

The arrangement 102 and the pump device 1a from FIG. 2 largely correspond to those from FIG. 1, and therefore reference is made to the comments presented in association therewith. Only the differences between the two exemplary embodiments according to FIGS. 1 and 2 will be addressed in the following.

In the exemplary embodiment according to FIG. 2, the detection unit 8 is not connected to control electronics (24; see FIG. 1, not shown in FIG. 2) of the operating table 20. Instead, the pump device 1a comprises a telemetry unit 10 having a telemetry transmitter 11 and a reference module 12.

The telemetry transmitter 11 is designed for determining, via a distance-measuring unit, the distance between itself and the reference module 12. The distance measurement takes place by means of a field-strength measurement of the electromagnetic field generated by the reference module 12, which is carried out by the distance-measuring unit.

Since the telemetry transmitter 11 is disposed on the height-adjustable part 22 of the operating table 20 and the reference module 12 is disposed on the base 23 of the operating table 20, the presently set height of the operating table 20 can be determined on the basis of the determined distance between the telemetry transmitter 11 and the reference module 12. The arrangement of the telemetry transmitter 11 and the reference module 12 can also be reversed.

The telemetry transmitter 11 comprises a radio antenna 14 which interacts with a radio antenna 9 disposed on the detection module 8, in order to exchange information between the telemetry transmitter 11 and the detection module 8. The telemetry transmitter 11 can deliver different pieces of output information in this case, which are directly comparable, such as, to the height-adjustment signal of the control electronics 24 from the first exemplary embodiment according to FIG. 1 and to output information regarding the absolute height of the operating table 20 from the control electronics 24 from the same exemplary embodiment. In order to generate a height-adjustment signal, the telemetry transmitter 11 can monitor the change in the absolute height or can comprise an acceleration sensor which records any acceleration in the vertical direction.

In the second exemplary embodiment, the detection module 8 of the pump device 1a likewise has two operating modes which can be set via the user interface 7. The operating modes in this case correspond to those from the first exemplary embodiment, wherein the output information originates only from the telemetry unit 10 and not from the control electronics 24 of the operating table 20. Reference is therefore made to the comments presented above.

FIG. 3 illustrates one variant of the exemplary embodiment from FIG. 2.

In the exemplary embodiment in FIG. 3, the arrangement 104 includes a pump device 1b in which the distance-measuring unit of the telemetry transmitter 11 is disposed on the height-adjustable part 22 of the operating table 20, which measures the distance to the floor 90 and to the ceiling 91 of the operating room. The distance measurement takes place in this case via a transit-time measurement of an electromagnetic wave outside the visible spectrum. The telemetry transmitter 11 transmits both distances as output information to the detection module 8. The detection module 8 carries out a validity check of the distances by comparing the sum of the distances with the distance between the floor 90 and the ceiling 91. If the aforementioned sum corresponds to this difference, the measured distances are considered to be valid and can be further processed. Reference is made to the comments associated with FIG. 2 in this regard.

In the variant according to FIG. 2, the pump device 1 additionally comprises a light source 15 which can be configured as a laser and is assigned to the detection module 8. The light source 15 projects a calibration plane 16 onto the patient who is lying on the operating table 20. The calibration plane 16 is projected, in this case, in such a way that the surroundings of the surgical site 5—i.e., the area around the point of insertion of the endoscope 4—are free from projections of the light element 15 in the initial height setting of the operating table 20, but when the height of the operating table 20 is adjusted downward, the projection moves into these surroundings which are typically within the field of view of the operating surgeon.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. A pump device for use with control electronics for operating an operating table in an operating room, the pump device comprising:
   a pump for pumping a rinsing liquid through a pump tube, and
   a controller configured to:
      receive a signal from the control electronics;
      detect a height adjustment of the operating table in the operating room based on the received signal;
      determine a height difference of the height adjustment; and
      change a pump pressure of the pump depending on the determined height difference.

2. The pump device according to claim 1 further comprising a telemetry unit having a telemetry transmitter configured to detect the height difference of the operating table, wherein the controller is configured to one of receive and request output information from the telemetry transmitter of the telemetry unit and to determine the height difference of the operating table based on the output information.

3. The pump device according to claim 2, wherein the telemetry unit comprises a detection-measuring unit and/or an acceleration sensor.

4. The pump device according to claim 1, wherein the controller is further configured to output one or more of an optical or acoustic warning signal upon the determination of the height adjustment of the operating table.

5. The pump device according to claim 1, wherein a relationship between the height difference and the change in the pump pressure is linear.

6. The pump device according to claim 5, wherein the pump pressure is determined according to the equation:
   where a change in the pump pressure is $\Delta p$, a correction factor is a, the height difference of the height adjustment is $\Delta h$ and a conversion factor is $$10^4 \frac{\text{Pa}}{\text{m}}.$$

7. The pump device according to claim 6, wherein the correction factor a is between 0.8 to 1.2.

8. The pump device according to claim 6, wherein the correction factor a is between 0.9 and 1.1.

9. The pump device according to claim 6, wherein the correction factor a is 1.

10. The pump device according to claim 1 wherein the controller controls a light element for projecting one of a calibration plane, a calibration scale and at least one calibration point onto one of the operating table and onto a patient lying on the operating table.

11. An arrangement for use in an operating room, the arrangement comprising:
    the pump device according to claim 1, and
    the operating table having the control electronics and further having a height adjustment capability.

* * * * *